United States Patent
Andreas et al.

(10) Patent No.: US 7,938,852 B2
(45) Date of Patent: *May 10, 2011

(54) APPARATUS AND METHODS FOR DELIVERY OF BRAIDED PROSTHESES

(75) Inventors: Bernard Andreas, Redwood City, CA (US); Ron French, Santa Clara, CA (US); Mark E. Deem, Mountain View, CA (US); Hanson S. Gifford, III, Woodside, CA (US); Allan Will, Atherton, CA (US)

(73) Assignee: Xtent, Inc., Menlo Park, CA (US)

( * ) Notice: Subject to any disclaimer, the term of this patent is extended or adjusted under 35 U.S.C. 154(b) by 9 days.

This patent is subject to a terminal disclaimer.

(21) Appl. No.: 12/040,598

(22) Filed: Feb. 29, 2008

(65) Prior Publication Data
US 2008/0147162 A1 Jun. 19, 2008

Related U.S. Application Data (63) Continuation of application No. 10/966,806, filed on Oct. 14, 2004, now Pat. No. 7,357,812, which is a continuation of application No. 10/306,620, filed on Nov. 27, 2002, now Pat. No. 7,147,656.

(60) Provisional application No. 60/336,607, filed on Dec. 3, 2001.

(51) Int. Cl.
*A61F 2/06* (2006.01)
(52) U.S. Cl. ....................................... 623/1.11
(58) Field of Classification Search ......... 623/1.11–1.58
See application file for complete search history.

(56) References Cited

U.S. PATENT DOCUMENTS

| | | | |
|---|---|---|---|
| 4,069,825 A | 1/1978 | Akiyama | |
| 4,468,224 A | 8/1984 | Enzmann et al. | |
| 4,512,338 A | 4/1985 | Balko | |
| 4,564,014 A | 1/1986 | Fogarty et al. | |
| 4,580,568 A | 4/1986 | Gianturco | |
| 4,681,110 A | 7/1987 | Wiktor | |
| 4,690,684 A | 9/1987 | McGreevy et al. | |
| 4,733,665 A | 3/1988 | Palmaz | |
| 4,739,762 A | 4/1988 | Palmaz | |
| 4,762,129 A | 8/1988 | Bonzel | |

(Continued)

FOREIGN PATENT DOCUMENTS
EP 0 203 945 B2 12/1986
(Continued)

OTHER PUBLICATIONS
Colombo, "The Invatec Bifurcation Stent Solution" Bifurcation Stents: Novel Solutions, TCT 2003, Washington: Sep. 15-19, 2003, 24 pages total.

(Continued)

*Primary Examiner* — Suzette J Gherbi
(74) *Attorney, Agent, or Firm* — Kilpatrick Townsend & Stockton, LLP (57) ABSTRACT

Blood vessels and other body lumens are expanded using an evertible braided prosthesis. The braided prosthesis is delivered to the blood vessel in a radially collapsed configuration. A leading edge of the braided prosthesis is then everted so that it expands as it is advanced through the blood vessel. Optionally, the prosthesis can be provided with a biologically active substance in order to inhibit hyperplasia or have other desired biological effects.

24 Claims, 2 Drawing Sheets

U.S. PATENT DOCUMENTS

| | | | |
|---|---|---|---|
| 4,770,176 A | 9/1988 | McGreevy et al. | |
| 4,775,337 A | 10/1988 | Van Wagener et al. | |
| 4,776,337 A | 10/1988 | Palmaz | |
| 4,886,062 A | 12/1989 | Wiktor | |
| 4,891,225 A | 1/1990 | Langer et al. | |
| 4,988,356 A | 1/1991 | Crittenden et al. | |
| 4,994,066 A | 2/1991 | Voss | |
| 4,994,069 A | 2/1991 | Ritchart et al. | |
| 5,013,318 A | 5/1991 | Spranza, III | |
| 5,040,548 A | 8/1991 | Yock | |
| 5,064,435 A | 11/1991 | Porter | |
| 5,092,877 A | 3/1992 | Pinchuk | |
| 5,102,417 A | 4/1992 | Palmaz | |
| 5,104,404 A | 4/1992 | Wolff | |
| 5,135,535 A | 8/1992 | Kramer | |
| 5,195,984 A | 3/1993 | Schatz | |
| 5,217,495 A | 6/1993 | Kaplan et al. | |
| 5,219,355 A | 6/1993 | Parodi et al. | |
| 5,226,913 A | 7/1993 | Pinchuk | |
| 5,246,421 A | 9/1993 | Saab | |
| 5,273,536 A | 12/1993 | Savas | |
| 5,282,824 A | 2/1994 | Gianturco | |
| 5,300,085 A | 4/1994 | Yock | |
| 5,312,415 A | 5/1994 | Palermo | |
| 5,334,187 A | 8/1994 | Fischell et al. | |
| 5,421,955 A | 6/1995 | Lau et al. | |
| 5,456,713 A | 10/1995 | Chuter | |
| 5,458,615 A | 10/1995 | Klemm et al. | |
| 5,478,349 A | 12/1995 | Nicholas | |
| 5,490,837 A | 2/1996 | Blaeser et al. | |
| 5,496,346 A | 3/1996 | Horzewski et al. | |
| 5,501,227 A | 3/1996 | Yock | |
| 5,507,768 A | 4/1996 | Lau et al. | |
| 5,507,771 A | 4/1996 | Gianturco | |
| 5,514,093 A | 5/1996 | Ellis et al. | |
| 5,514,154 A | 5/1996 | Lau et al. | |
| 5,527,354 A | 6/1996 | Fontaine et al. | |
| 5,549,551 A | 8/1996 | Peacock, III et al. | |
| 5,549,563 A | 8/1996 | Kronner | |
| 5,549,635 A | 8/1996 | Solar | |
| 5,554,181 A | 9/1996 | Das | |
| 5,562,725 A | 10/1996 | Schmitt et al. | |
| 5,571,086 A | 11/1996 | Kaplan et al. | |
| 5,593,412 A | 1/1997 | Martinez et al. | |
| 5,607,444 A | 3/1997 | Lam | |
| 5,607,463 A | 3/1997 | Schwartz et al. | |
| 5,628,775 A | 5/1997 | Jackson et al. | |
| 5,634,928 A | 6/1997 | Fischell et al. | |
| 5,639,274 A | 6/1997 | Fischell et al. | |
| 5,662,675 A | 9/1997 | Polanskyj Stockert et al. | |
| 5,670,161 A | 9/1997 | Healy et al. | |
| 5,676,654 A | 10/1997 | Ellis et al. | |
| 5,683,451 A | 11/1997 | Lenker et al. | |
| 5,697,948 A | 12/1997 | Marin et al. | |
| 5,702,418 A | 12/1997 | Ravenscroft | |
| 5,709,701 A | 1/1998 | Parodi | |
| 5,716,393 A | 2/1998 | Lindenberg et al. | |
| 5,722,669 A | 3/1998 | Shimizu et al. | |
| 5,723,003 A | 3/1998 | Winston et al. | |
| 5,735,869 A | 4/1998 | Fernandez-Aceytuno | |
| 5,741,323 A | 4/1998 | Pathak et al. | |
| 5,749,848 A | 5/1998 | Jang et al. | |
| 5,749,921 A | 5/1998 | Lenker et al. | |
| 5,755,772 A | 5/1998 | Evans et al. | |
| 5,755,776 A | 5/1998 | Al-Saadon | |
| 5,755,781 A | 5/1998 | Jayaraman | |
| 5,769,882 A | 6/1998 | Fogarty et al. | |
| 5,772,669 A | 6/1998 | Vrba | |
| 5,776,141 A | 7/1998 | Klein et al. | |
| 5,797,951 A | 8/1998 | Mueller et al. | |
| 5,800,519 A | 9/1998 | Sandock | |
| 5,807,398 A | 9/1998 | Shaknovich | |
| 5,824,040 A | 10/1998 | Cox et al. | |
| 5,824,041 A | 10/1998 | Lenker et al. | |
| 5,833,694 A | 11/1998 | Poncet | |
| 5,836,964 A | 11/1998 | Richter et al. | |
| 5,843,092 A | 12/1998 | Heller et al. | |
| 5,855,563 A | 1/1999 | Kaplan et al. | |
| 5,858,556 A | 1/1999 | Eckert et al. | |
| 5,870,381 A | 2/1999 | Kawasaki et al. | |
| 5,879,370 A | 3/1999 | Fischell et al. | |
| 5,891,190 A | 4/1999 | Boneau | |
| 5,895,398 A | 4/1999 | Wensel et al. | |
| 5,899,935 A | 5/1999 | Ding | |
| 5,902,332 A | 5/1999 | Schatz | |
| 5,919,175 A | 7/1999 | Sirhan | |
| 5,922,020 A | 7/1999 | Klein et al. | |
| 5,961,536 A | 10/1999 | Mickley et al. | |
| 5,968,069 A | 10/1999 | Dusbabek et al. | |
| 5,976,107 A | 11/1999 | Mertens et al. | |
| 5,976,155 A | 11/1999 | Foreman et al. | |
| 5,980,484 A | 11/1999 | Ressemann et al. | |
| 5,980,486 A | 11/1999 | Enger | |
| 5,980,514 A | 11/1999 | Kupiecki et al. | |
| 5,980,552 A | 11/1999 | Pinchasik et al. | |
| 5,984,957 A | 11/1999 | Laptewicz, Jr. et al. | |
| 5,997,563 A | 12/1999 | Kretzers et al. | |
| 6,004,328 A | 12/1999 | Solar | |
| 6,007,517 A | 12/1999 | Anderson | |
| 6,022,359 A | 2/2000 | Frantzen | |
| 6,022,374 A | 2/2000 | Imran | |
| 6,033,434 A | 3/2000 | Borghi | |
| 6,039,721 A | 3/2000 | Johnson et al. | |
| 6,042,589 A | 3/2000 | Marianne | |
| 6,056,722 A | 5/2000 | Jayaraman | |
| 6,066,155 A | 5/2000 | Amann et al. | |
| 6,068,655 A | 5/2000 | Seguin et al. | |
| 6,070,589 A | 6/2000 | Keith et al. | |
| 6,090,063 A | 7/2000 | Makower et al. | |
| 6,090,136 A | 7/2000 | McDonald et al. | |
| 6,102,942 A | 8/2000 | Ahari | |
| 6,106,530 A | 8/2000 | Harada | |
| RE36,857 E | 9/2000 | Euteneuer et al. | |
| 6,120,522 A | 9/2000 | Vrba et al. | |
| 6,123,712 A | 9/2000 | Di Caprio et al. | |
| 6,123,723 A | 9/2000 | Konya et al. | |
| 6,126,685 A | 10/2000 | Lenker et al. | |
| 6,129,756 A | 10/2000 | Kugler | |
| 6,132,460 A | 10/2000 | Thompson | |
| 6,143,016 A | 11/2000 | Bleam et al. | |
| 6,165,167 A | 12/2000 | Delaloye | |
| 6,165,210 A | 12/2000 | Lau et al. | |
| 6,179,878 B1 | 1/2001 | Duering | |
| 6,183,509 B1 | 2/2001 | Dibie | |
| 6,187,034 B1 | 2/2001 | Frantzen | |
| 6,190,402 B1 | 2/2001 | Horton et al. | |
| 6,196,995 B1 | 3/2001 | Fagan | |
| 6,200,337 B1 | 3/2001 | Moriuchi et al. | |
| 6,238,991 B1 | 5/2001 | Suzuki | |
| 6,241,691 B1 | 6/2001 | Ferrera et al. | |
| 6,251,132 B1 | 6/2001 | Ravenscroft et al. | |
| 6,251,134 B1 | 6/2001 | Alt et al. | |
| 6,254,612 B1 | 7/2001 | Hieshima | |
| 6,254,628 B1 | 7/2001 | Wallace et al. | |
| 6,258,117 B1 | 7/2001 | Camrud et al. | |
| 6,264,688 B1 | 7/2001 | Herklotz et al. | |
| 6,267,783 B1 | 7/2001 | Letendre et al. | |
| 6,273,895 B1 | 8/2001 | Pinchuk et al. | |
| 6,273,911 B1 | 8/2001 | Cox et al. | |
| 6,273,913 B1 | 8/2001 | Wright et al. | |
| 6,312,458 B1 | 11/2001 | Golds | |
| 6,315,794 B1 | 11/2001 | Richter | |
| 6,319,277 B1 | 11/2001 | Rudnick et al. | |
| 6,322,586 B1 | 11/2001 | Monroe et al. | |
| 6,325,823 B1 | 12/2001 | Horzewski et al. | |
| 6,334,871 B1 | 1/2002 | Dor et al. | |
| 6,342,068 B1 * | 1/2002 | Thompson | 623/1.53 |
| 6,344,272 B1 | 2/2002 | Oldenburg et al. | |
| 6,357,104 B1 | 3/2002 | Myers | |
| 6,375,676 B1 | 4/2002 | Cox | |
| 6,379,365 B1 | 4/2002 | Diaz | |
| 6,383,171 B1 * | 5/2002 | Gifford et al. | 604/508 |
| 6,409,750 B1 * | 6/2002 | Hyodoh et al. | 623/1.1 |
| 6,409,753 B1 | 6/2002 | Brown et al. | |
| 6,415,696 B1 | 7/2002 | Erickeson et al. | |
| 6,419,693 B1 | 7/2002 | Fariabi | |
| 6,428,811 B1 | 8/2002 | West et al. | |

| | | | | | | |
|---|---|---|---|---|---|---|
| 6,451,025 B1 | 9/2002 | Jervis | | 7,220,755 B2 | 5/2007 | Betts et al. |
| 6,451,050 B1 | 9/2002 | Rudakov et al. | | 7,241,308 B2 | 7/2007 | Andreas et al. |
| 6,464,720 B2 | 10/2002 | Boatman et al. | | 7,244,336 B2 | 7/2007 | Fischer et al. |
| 6,468,298 B1 | 10/2002 | Pelton | | 7,270,668 B2 | 9/2007 | Andreas et al. |
| 6,468,299 B2 | 10/2002 | Stack et al. | | 7,294,146 B2 | 11/2007 | Chew et al. |
| 6,485,510 B1 | 11/2002 | Camrud et al. | | 7,300,456 B2 | 11/2007 | Andreas et al. |
| 6,488,694 B1 | 12/2002 | Lau et al. | | 7,309,350 B2 | 12/2007 | Landreville et al. |
| 6,488,702 B1 | 12/2002 | Besselink | | 7,314,480 B2 | 1/2008 | Eidenschink et al. |
| 6,511,468 B1 | 1/2003 | Cragg et al. | | 7,320,702 B2 | 1/2008 | Hammersmark et al. |
| 6,520,986 B2 | 2/2003 | Martin et al. | | 7,323,006 B2 | 1/2008 | Andreas et al. |
| 6,520,987 B1 | 2/2003 | Plante | | 7,326,236 B2 | 2/2008 | Andreas et al. |
| 6,527,789 B1 | 3/2003 | Lau et al. | | 7,351,255 B2 | 4/2008 | Andreas |
| 6,527,799 B2 | 3/2003 | Shanley | | 2001/0020154 A1 | 9/2001 | Bigus et al. |
| 6,530,944 B2 | 3/2003 | West et al. | | 2001/0020181 A1 | 9/2001 | Layne |
| 6,540,777 B2 | 4/2003 | Stenzel | | 2001/0044595 A1 | 11/2001 | Reydel et al. |
| 6,551,350 B2 | 4/2003 | Thornton et al. | | 2001/0049547 A1 | 12/2001 | Moore |
| 6,555,157 B1 | 4/2003 | Hossainy | | 2002/0037358 A1 | 3/2002 | Barry et al. |
| 6,569,180 B1 | 5/2003 | Sirhan et al. | | 2002/0107560 A1 | 8/2002 | Richter |
| 6,575,993 B1 | 6/2003 | Yock | | 2002/0111671 A1 | 8/2002 | Stenzel |
| 6,579,305 B1 | 6/2003 | Lashinski | | 2002/0128706 A1 | 9/2002 | Ospyka |
| 6,579,309 B1 | 6/2003 | Loos et al. | | 2002/0138132 A1 | 9/2002 | Brown |
| 6,582,394 B1 | 6/2003 | Reiss et al. | | 2002/0151924 A1 | 10/2002 | Shiber |
| 6,582,460 B1 | 6/2003 | Cryer | | 2002/0151955 A1 | 10/2002 | Tran et al. |
| 6,585,756 B1 | 7/2003 | Strecker | | 2002/0156496 A1 | 10/2002 | Chermoni |
| 6,592,549 B2 | 7/2003 | Gerdts et al. | | 2002/0177890 A1 | 11/2002 | Lenker |
| 6,599,296 B1 | 7/2003 | Gillick et al. | | 2002/0183763 A1 | 12/2002 | Callol et al. |
| 6,599,314 B2 | 7/2003 | Mathis | | 2002/0188343 A1 | 12/2002 | Mathis |
| 6,602,282 B1 | 8/2003 | Yan | | 2002/0188347 A1 | 12/2002 | Mathis |
| 6,605,062 B1 | 8/2003 | Hurley et al. | | 2002/0193873 A1 | 12/2002 | Brucker et al. |
| 6,605,109 B2 | 8/2003 | Fiedler | | 2003/0045923 A1 | 3/2003 | Bashiri et al. |
| 6,607,553 B1 | 8/2003 | Healy et al. | | 2003/0093143 A1 | 5/2003 | Zhao et al. |
| 6,645,517 B2 | 11/2003 | West | | 2003/0097169 A1 | 5/2003 | Brucker et al. |
| 6,645,547 B1 | 11/2003 | Shekalim et al. | | 2003/0114912 A1 | 6/2003 | Sequin et al. |
| 6,656,212 B2 | 12/2003 | Ravenscroft et al. | | 2003/0114919 A1 | 6/2003 | McQuiston et al. |
| 6,660,031 B2 | 12/2003 | Tran et al. | | 2003/0114922 A1 | 6/2003 | Iwasaka et al. |
| 6,660,381 B2 | 12/2003 | Halas et al. | | 2003/0125791 A1 | 7/2003 | Sequin et al. |
| 6,666,883 B1 | 12/2003 | Seguin et al. | | 2003/0125800 A1 | 7/2003 | Shulze et al. |
| 6,676,695 B2 | 1/2004 | Solem | | 2003/0125802 A1 | 7/2003 | Callol et al. |
| 6,679,909 B2 | 1/2004 | McIntosh et al. | | 2003/0135259 A1 | 7/2003 | Simso |
| 6,685,730 B2 | 2/2004 | West et al. | | 2003/0135266 A1 | 7/2003 | Chew et al. |
| 6,692,465 B2 | 2/2004 | Kramer | | 2003/0139796 A1 | 7/2003 | Sequin et al. |
| 6,699,280 B2 | 3/2004 | Camrud et al. | | 2003/0139797 A1 | 7/2003 | Johnson et al. |
| 6,699,724 B1 | 3/2004 | West et al. | | 2003/0139798 A1 | 7/2003 | Brown et al. |
| 6,702,843 B1 | 3/2004 | Brown | | 2003/0163085 A1 | 8/2003 | Tanner et al. |
| 6,709,379 B1 | 3/2004 | Brandau et al. | | 2003/0176909 A1 | 9/2003 | Kusleika |
| 6,709,440 B2 | 3/2004 | Callol et al. | | 2003/0191516 A1 | 10/2003 | Weldon et al. |
| 6,712,827 B2 | 3/2004 | Ellis et al. | | 2003/0195609 A1 | 10/2003 | Berenstein |
| 6,712,845 B2 | 3/2004 | Hossainy | | 2003/0199821 A1 | 10/2003 | Gerdts et al. |
| 6,723,071 B2 | 4/2004 | Gerdts et al. | | 2003/0204238 A1 | 10/2003 | Tedeschi |
| 6,736,842 B2 | 5/2004 | Healy et al. | | 2003/0212447 A1 | 11/2003 | Euteneuer |
| 6,743,251 B1 | 6/2004 | Eder | | 2003/0225446 A1 | 12/2003 | Hartley |
| 6,761,734 B2 | 7/2004 | Suhr | | 2004/0024450 A1 | 2/2004 | Shulze et al. |
| 6,778,316 B2 | 8/2004 | Halas et al. | | 2004/0030380 A1 | 2/2004 | Shulze et al. |
| 6,800,065 B2 | 10/2004 | Duane et al. | | 2004/0044395 A1 | 3/2004 | Nelson |
| 6,825,203 B2 | 11/2004 | Pasternak et al. | | 2004/0093061 A1 | 5/2004 | Acosta et al. |
| 6,837,901 B2 | 1/2005 | Rabkin et al. | | 2004/0106979 A1 | 6/2004 | Goicoechea |
| 6,849,084 B2 | 2/2005 | Rabkin et al. | | 2004/0117008 A1 | 6/2004 | Wnendt et al. |
| 6,852,252 B2 | 2/2005 | Halas et al. | | 2004/0176832 A1 | 9/2004 | Hartley et al. |
| 6,855,125 B2 | 2/2005 | Shanley | | 2004/0186551 A1 | 9/2004 | Kao et al. |
| 6,858,034 B1 | 2/2005 | Hijlkema et al. | | 2004/0193245 A1 | 9/2004 | Deem et al. |
| 6,878,161 B2 | 4/2005 | Lenker | | 2004/0215312 A1 | 10/2004 | Andreas et al. |
| 6,893,417 B2 | 5/2005 | Gribbons et al. | | 2004/0249434 A1 | 12/2004 | Andreas et al. |
| 6,899,728 B1 * | 5/2005 | Phillips et al. ............... 623/1.13 | | 2005/0010276 A1 | 1/2005 | Acosta et al. |
| 6,918,928 B2 | 7/2005 | Wolinsky et al. | | 2005/0038505 A1 | 2/2005 | Shulze et al. |
| 6,939,376 B2 | 9/2005 | Shulz et al. | | 2005/0049673 A1 | 3/2005 | Andreas et al. |
| 6,945,989 B1 | 9/2005 | Betelia et al. | | 2005/0080474 A1 | 4/2005 | Andreas et al. |
| 6,951,053 B2 | 10/2005 | Padilla et al. | | 2005/0080475 A1 | 4/2005 | Andreas et al. |
| 6,994,721 B2 | 2/2006 | Israel | | 2005/0090846 A1 | 4/2005 | Pedersen et al. |
| 7,005,454 B2 | 2/2006 | Brocchini et al. | | 2005/0125051 A1 | 6/2005 | Eidenschink et al. |
| 7,090,694 B1 | 8/2006 | Morris et al. | | 2005/0131008 A1 | 6/2005 | Betts et al. |
| 7,101,840 B2 | 9/2006 | Brocchini et al. | | 2005/0143827 A1 | 6/2005 | Globerman et al. |
| 7,137,993 B2 | 11/2006 | Acosta et al. | | 2005/0209674 A1 | 9/2005 | Kutscher et al. |
| 7,141,063 B2 | 11/2006 | White et al. | | 2005/0222671 A1 | 10/2005 | Schaeffer et al. |
| 7,147,655 B2 | 12/2006 | Chermoni | | 2005/0228477 A1 | 10/2005 | Grainger et al. |
| 7,147,656 B2 | 12/2006 | Andreas et al. | | 2005/0245637 A1 | 11/2005 | Hossainy et al. |
| 7,169,172 B2 | 1/2007 | Levine et al. | | 2005/0288764 A1 | 12/2005 | Snow et al. |
| 7,182,779 B2 | 2/2007 | Acosta et al. | | 2005/0288766 A1 | 12/2005 | Plain et al. |
| 7,192,440 B2 | 3/2007 | Andreas et al. | | 2006/0069424 A1 | 3/2006 | Acosta et al. |
| 7,208,001 B2 | 4/2007 | Coyle et al. | | 2006/0200223 A1 | 9/2006 | Andreas et al. |

| | | |
|---|---|---|
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2007/0027521 A1 | 2/2007 | Andreas et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0132989 A1 | 6/2008 | Snow et al. |
| 2008/0147162 A1 | 6/2008 | Andreas et al. |
| 2008/0199510 A1 | 8/2008 | Ruane et al. |

FOREIGN PATENT DOCUMENTS

| | | |
|---|---|---|
| EP | 0 274 129 B1 | 7/1988 |
| EP | 0 282 143 | 9/1988 |
| EP | 0 505 686 | 9/1992 |
| EP | 0 533 960 | 3/1993 |
| EP | 0 714 640 | 6/1996 |
| EP | 0 596 145 | 5/1997 |
| EP | 0 947 180 | 10/1999 |
| EP | 1 258 230 | 11/2002 |
| EP | 1 266 638 B1 | 12/2002 |
| EP | 1 277 449 | 1/2003 |
| EP | 1 318 765 | 6/2003 |
| EP | 1 523 959 A2 | 4/2005 |
| EP | 1 523 960 A2 | 4/2005 |
| WO | WO 96/33677 | 10/1996 |
| WO | WO 97/46174 | 12/1997 |
| WO | WO 97/48351 | 12/1997 |
| WO | WO 98/37833 | 9/1998 |
| WO | WO 99/01087 | 1/1999 |
| WO | WO 00/12832 A3 | 3/2000 |
| WO | WO 00/15151 | 3/2000 |
| WO | WO 00/25841 | 5/2000 |
| WO | WO 00/32136 | 6/2000 |
| WO | WO 00/41649 | 7/2000 |
| WO | WO 00/50116 | 8/2000 |
| WO | WO 00/62708 | 10/2000 |
| WO | WO 00/72780 | 12/2000 |
| WO | WO 01/70297 | 9/2001 |
| WO | WO 01/91918 | 12/2001 |
| WO | WO 02/085253 | 10/2002 |
| WO | WO 03/022178 | 3/2003 |
| WO | WO 03/047651 | 6/2003 |
| WO | WO 03/051425 | 6/2003 |
| WO | WO 03/075797 | 9/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 A2 | 6/2004 |
| WO | WO 2005/013853 | 2/2005 |
| WO | WO 2007/146411 | 12/2007 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," Journal of Controlled Release 92 (2003) pp. 83-91.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., Parallel Production of Oligonucleotide Arrays Using Membranes and Reagent Jet Printing, BioTechniques 25:886-890 (Nov. 1998).

Supplementary European Search Report of EP Patent Application No. 05727731.1, dated Mar. 25, 2008, 2 pages total.

Supplementary European Search Report of EP Patent Application No. 05744136, dated Mar. 26, 2008, 3 pages total.

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

U.S. Appl. No. 61/012,317, filed Dec. 7, 2007, first named inventor: Patrick Ruane.

U.S. Appl. No. 09/097,855, filed Jun. 15, 1998, first named inventor: Enrique J. Klein; Abandoned.

U.S. Appl. No. 09/225,364, filed Jan. 4, 1999, first named inventor: Aaron V. Kaplan; abandoned.

U.S. Appl. No. 10/874,859, filed Jun. 22, 2004, first named inventor: Pablo Acosta. Abandoned.

U.S. Appl. No. 11/462,951, filed Aug. 7, 2006, first named inventor: David Snow.

U.S. Appl. No. 11/627,096, filed Jan. 25, 2007, first named inventor: Bernard Andreas.

U.S. Appl. No. 11/689,927, filed Mar. 22, 2007, first named inventor: David Snow.

U.S. Appl. No. 11/752,448, filed May 23, 2007, first named inventor: David Snow.

U.S. Appl. No. 11/771,929, filed Jun. 29, 2007, first named inventor: David Snow.

U.S. Appl. No. 11/857,562, filed Sep. 19, 2007, first named inventor: Bryan Mao.

U.S. Appl. No. 11/938,730, filed Nov. 12, 2007, first named inventor: Sunmi Chew.

U.S. Appl. No. 11/945,142, filed Nov. 26, 2007, first named inventor: Bernard Andreas.

U.S. Appl. No. 11/947,677, filed Nov. 29, 2007, first named inventor: Dan Hammersmark.

U.S. Appl. No. 11/952,644, filed Dec. 7, 2007, first named inventor: Bernard Andreas.

U.S. Appl. No. 12/043,513, filed Mar. 6, 2008, first named inventor: David Lowe.

U.S. Appl. No. 12/057,527, filed Mar. 28, 2008, first named inventor: Allan Will.

U.S. Appl. No. 12/061,951, filed Apr. 3, 2008, first named inventor: Stephen Kao.

U.S. Appl. No. 12/109,477, filed Apr. 25, 2008, first named inventor: Stephen Kao.

U.S. Appl. No. 12/127,147, filed May 27, 2008, first named inventor: Sunmi Chew.

U.S. Appl. No. 12/133,909, filed Jun. 5, 2008, first named inventor: David Sanderson.

* cited by examiner

APPARATUS AND METHODS FOR DELIVERY OF BRAIDED PROSTHESES

CROSS-REFERENCES TO RELATED APPLICATIONS

The present application is a continuation of U.S. patent application Ser. No. 10/966,806, filed Oct. 14, 2004 (now U.S. Pat. No. 7,357,812), which is a continuation of U.S. patent application Ser. No. 10/306,620, filed Nov. 27, 2002 (now U.S. Pat. No. 7,147,656), which claims priority to U.S. Provisional Patent Application Ser. No. 60/336,607, filed Dec. 3, 2001, the full disclosures of which are incorporated herein by reference.

BACKGROUND OF THE INVENTION

1. Field of the Invention

The present invention relates generally to medical devices and methods. More particularly, the present invention relates to apparatus and methods for delivering braided and other everting prostheses within a body lumen, such as a blood vessel.

Coronary artery disease is the leading cause of death and morbidity in the United States and Western society. In particular, atherosclerosis in the coronary arteries can cause myocardial infarction, commonly referred to as a heart attack, which can be immediately fatal or even if survived, cause damage to the heart which can incapacitate the patient.

While coronary artery bypass surgery can be an effective treatment for stenosed arteries resulting from atherosclerosis or other causes, it is a highly invasive, costly procedure, which typically requires substantial hospital and recovery time. Percutaneous transluminal coronary angioplasty, commonly referred to as balloon angioplasty, is less invasive, less traumatic, and significantly less expensive than bypass surgery. Heretofore, however, balloon angioplasty has not been considered as effective a treatment as bypass surgery. The effectiveness of balloon angioplasty, however, has improved significantly with the introduction of stenting, which involves the placement of a scaffold structure within the artery which has been treated by balloon angioplasty. The stent inhibits abrupt reclosure of the artery and has some benefit in inhibiting subsequent restenosis resulting from hyperplasia. Recently, experimental trials have demonstrated that coating stents with anti-proliferative drugs, such as paclitaxel, can significantly reduce the occurrence of hyperplasia in angioplasty treated coronary arteries which have been stented with the coated stents.

While the combination of balloon angioplasty with drug-coated stents holds great promise, significant challenges still remain. Of particular interest to the present invention, the treatment of extended or disseminated disease within an artery remains problematic. Most stents have a fixed length, typically in the range from 10 mm to 30 mm, and the placement of multiple stents to treat disease over a longer length requires the successive use of multiple balloon stent delivery catheters. Moreover, it can be difficult to stent an angioplasty-treated region of a blood vessel with the optimum stent length.

For these reasons, it would be desirable to provide improved stents, stent delivery systems, stenting methods, and the like, for the treatment of patients having coronary artery disease, as well as other occlusive diseases of the vasculature and other body lumens. In particular, it would be desirable to provide stents, delivery systems, and methods for the treatment of disseminated and variable length stenotic regions within the vasculature. For example, it would be desirable to provide a practical method which permits a physician to deliver extended lengths of braided prostheses to blood vessels and other body lumens. At least some of these objectives will be met by the inventions described hereinafter.

2. Description of the Background Art

U.S. Pat. No. 5,755,772 describes a tubular prosthesis and method for its implantation by positioning the prosthesis at a target site, and everting an end section to lock the stent after expansion has been completed; and U.S. Pat. No. 5,769,882 describes conformable tubular prostheses and their placement in blood vessels.

BRIEF SUMMARY OF THE INVENTION

The present invention provides methods and apparatus for the stenting of body lumens, typically blood vessels, and more typically coronary arteries. The methods and systems will also find significant use in the peripheral vasculature, the cerebral vasculature, and in other ducts, such as the biliary duct, the fallopian tubes, and the like. The terms "stent" and "stenting" are defined to include any of the wide variety of expandable scaffolds which are designed to be intraluminally introduced to a treatment site and expanded in situ to apply a radially outward force against the inner wall of the body lumen at that site. Stents commonly comprise an open lattice structure, typically formed from a malleable or elastic metal.

The stents of the present invention will comprise evertible structures which radially expand upon eversion to assume a non-collapsible diameter which remains in place within the body lumen to support the luminal wall. Typically, the evertible stent structures will comprise braided structures, but other structures, such as counterwound helices, will also be capable of eversion. In some instances, laser cut helical and other patterned metal tubes, particularly those formed from nickel titanium and other shape memory alloys, may be used. Thin wall tubes formed from polymeric materials, such as polyethylene terephthalate (PET), expanded polytetrafluoroethylene (e PTFE), may also find use, even without patterning.

The braided and other evertible stent structures of the present invention may be formed from metals, including both malleable metals and elastic metals, such as shape memory metals, as well as from polymeric materials. Usually, the braided structures will comprise individual ribbons of the desired material which are interwoven to form a braid so that the braid may be axially elongated to assume a narrow diameter configuration and thereafter be everted to assume a larger diameter configuration. By "evert" it is meant that a leading edge of the prosthesis is turned outwardly and backwardly relative to the narrow diameter portion thereof. In the preferred methods and apparatus of the present invention, as described in more detail below, such eversion will be achieved by initially holding the prosthesis in its narrow diameter configuration with the leading portion everted and fixed to an outer portion of a catheter. This leading portion is referred to as the "fixed end." The remainder of the prosthesis which remains in its narrow diameter configuration is held within a passage or lumen of a delivery catheter, and means are provided for pushing the "advanceable end" of the prosthesis which is in the lumen forwardly relative to the fixed end. In this way, the leading edge of the prosthesis moves forward continuously relative to the fixed end as it everts radially outwardly.

The use of such braided and other evertible prostheses provides a number of advantages. For example, the braided structure is highly flexible, particularly in its narrow diameter configuration, allowing the introduction of relatively long stent segments without significantly limiting the ability of the delivery catheter to pass through torturous regions of the vasculature or other body lumens. Additionally, by everting the prosthesis so that its outer portion remains stationary relative to the fixed end (and thus also relative to the delivery catheter), the stent will be able to pass through relatively small body lumens since it advances much like a tractor tread in moving forwardly through the lumen. In the case of vascular treatments, the stents of the present invention will usually be used following other primary interventions, such as angioplasty, atherectomy, aneurysm repair, or the like. It will be possible, however, in certain instances, to deliver the stent without prior intervention because of the ability to advance through tight lesions and to dilate the lesion as it passes therethrough.

Usually, the methods and apparatus of the present invention will be used to deliver a single stent having a predetermined length. In other instances, however, it will be possible to provide a means for severing the stent on the catheter itself. In such cases, the methods and apparatus of the present invention will be capable of delivering variable lengths of stent depending on the nature and extent of the disease being treated. That is, the apparatus will be used to deliver the stent under fluoroscopic or other observation, and after a desired length of stent has been deployed, the deployed length can be severed from the length which remains carried within the delivery catheter.

In one aspect of the present invention, a method for delivering a prosthesis to a body lumen comprises positioning a metallic tubular prosthesis at a target site within the body lumen. The prosthesis is then everted so that an inside surface is exposed radially outwardly and advanced over a length of the wall of the body lumen. Usually, positioning comprises introducing a delivery catheter having a passage which carries the tubular prosthesis at least partly in a radially collapsed configuration. Everting usually comprises pushing the tubular prosthesis from the catheter so that a leading portion of the prosthesis everts and radially expands as it exits the catheter or passage. This is usually accomplished by forwardly advancing a portion of the catheter to push the prosthesis from the catheter. In a preferred aspect of the present invention, an advanceable segment of the prosthesis is carried in the passage in the radially collapsed configuration. A fixed end of the prosthesis is held stationary relative to the catheter in a partially everted configuration. Everting then comprises pushing a proximal end (i.e., an end or portion of the prosthesis which is radially collapsed within the delivery catheter) to cause a middle portion of the prosthesis to progressively evert and advance distally relative to the fixed end. In the case of braided prostheses, the braided structure will shorten as the radius expands so that the "advanceable" proximal end prosthesis is pushed forward at a rate which is faster than the rate at which the everted prosthesis covers the wall of the body lumen. In preferred embodiments, the prosthesis releases an active substance which inhibits hyperplasia after the prosthesis has been placed in the body lumen.

In another aspect of the present invention, a method for delivering a stent to a blood vessel comprises positioning the stent at a target site within the blood vessel and everting the stent so that an inside surface is exposed radially outwardly and advanced over a length of a wall of the blood vessel. The stent, in turn, inhibits restenosis in the blood vessel.

In another aspect of the present invention, a method for delivering a prosthesis to a body lumen involves positioning a tubular prosthesis at a target site within the body lumen, the tubular prosthesis having a total length. The tubular prosthesis is then everted so that an inside surface is exposed radially outwardly and a desired length of the tubular prosthesis is advanced over a length of a wall of the body lumen, the desired length being less than the total length. The method then includes severing a portion of the tubular prosthesis having the desired length to allow the portion to remain in the body lumen.

In another aspect of the present invention, a method for delivering a prosthesis to a body lumen involves positioning a delivery catheter carrying a tubular prosthesis at a target site within the body lumen, everting the tubular prosthesis so that an inside surface is exposed radially outwardly and advanced over a desired length of a wall of the body lumen, and deploying a portion of the tubular prosthesis having the desired length. A second length of the tubular prosthesis remains carried within the delivery catheter.

In another aspect of the present invention, an apparatus for delivering a prosthesis to a body lumen includes a catheter having a passage, a metallic tubular prosthesis carried in the passage at least partially in a radially collapsed configuration, and a slidable member in the catheter for advancing the prosthesis from the passage so that the prosthesis everts and radially expands as it is advanced. In some embodiments, the metallic tubular prosthesis is a shape memory metal. In some embodiments, the metallic tubular prosthesis comprises a braided metal structure. Alternatively, the metallic tubular prosthesis may comprise an open lattice structure.

In yet another embodiment of the present invention, an apparatus for delivering a prosthesis to a blood vessel includes a catheter having a passage, a stent carried in the passage at least partially in a radially collapsed configuration, and a slidable member in the catheter for advancing the prosthesis from the passage so that said prosthesis everts and radially expands as it is advanced. The stent is configured to inhibit restenosis in the blood vessel.

In another aspect of the invention, an apparatus for delivering a prosthesis to a body lumen includes a catheter having a passage, a tubular prosthesis carried in the passage at least partially in a radially collapsed configuration, a slidable member in the catheter for advancing the prosthesis from the passage so that said prosthesis everts and radially expands as it is advanced, and a severing member in the catheter for severing a portion of the prosthesis to allow the portion to remain in the body lumen while a second portion of the prosthesis remains carried in the catheter.

These and other aspects and embodiments of the present invention will be described in further detail below, with reference to the attached drawing figures.

DETAILED DESCRIPTION OF THE INVENTION

Figure 1:
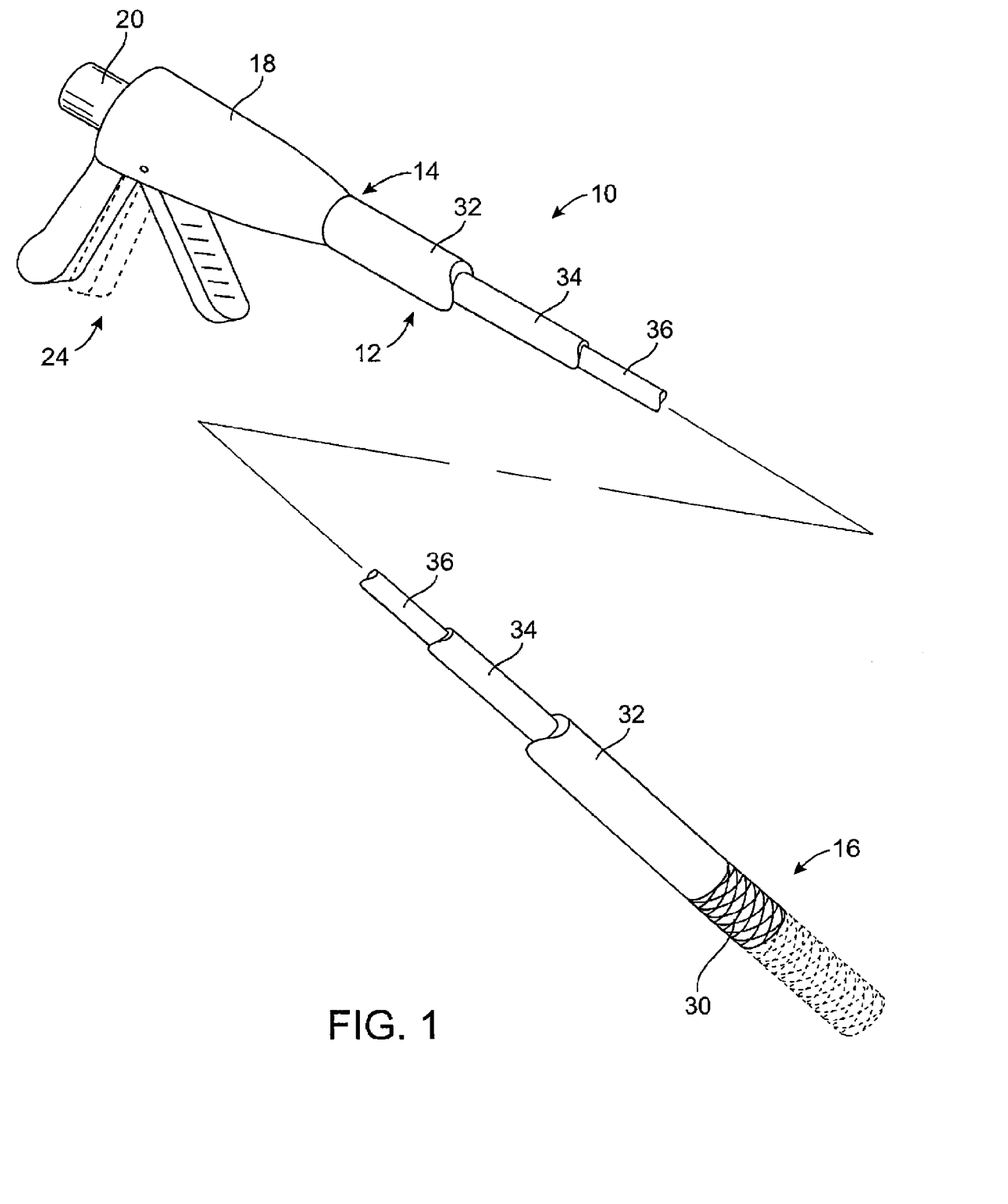
FIG. 1 is a perspective view illustrating a stent delivery catheter constructed in accordance with the principles of the present invention.

Referring now to FIG. 1, the stent delivery catheter 10 comprises a catheter body 12 having a proximal end 14 and a distal end 16. The catheter body 12 is formed from a conventional catheter material, such as a natural or synthetic polymer, such as silicone rubber, polyethylene, polyvinylchloride, polyurethane, polyester, polytetrafluoroethylene, nylon, and the like. The body may be formed as a composite having one or more reinforcement layers incorporated within a polymeric shell in order to enhance strength, flexibility, and toughness. For intravascular use, the catheter body will typically have a length in the range from 40 cm to 150 cm, usually being between 40 cm and 120 cm for peripheral blood vessels and between 110 cm and 150 cm for coronary arteries. The outer diameter of the catheter body may vary depending on the intended use, typically being between 3 French and 15 French, usually from 5 French to 9 French (one French=0.33 mm).

Catheter 10 further comprises a handle 18 at its proximal end 14. The handle has a guidewire port 20 at its distal end as well as a handle grip 24 which is actuable to extend and release evertible prosthesis 30 from the distal end 16. The catheter body 12 comprises an outer tube 32, a middle tube 34 which is coaxially and slidably mounted within a lumen of the outer tube 32, and an inner tube 36 which is slidably and coaxially mounted within a lumen of the middle tube 34. Inner tube 36 has a central lumen for receiving a guidewire, as described in detail below.

Figure 2A:
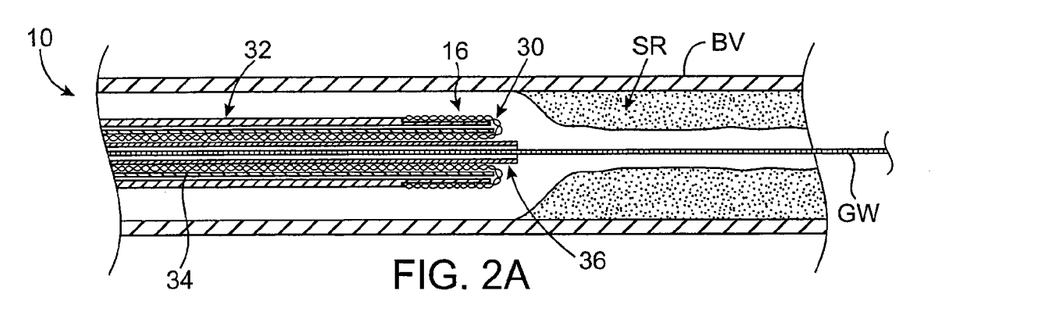
FIGS. 2A-2D illustrate use of the catheter in FIG. 1 for deploying a braided stent within a stenosed region in a blood vessel.

Referring now to FIGS. 2A-2D, delivery of the prosthesis 30 within a stenosed region SR of a blood vessel BV is described. The distal end 16 of the catheter 10 is introduced over a guidewire GW to the stenosed region SR as shown in FIG. 2A.

Figure 2B:
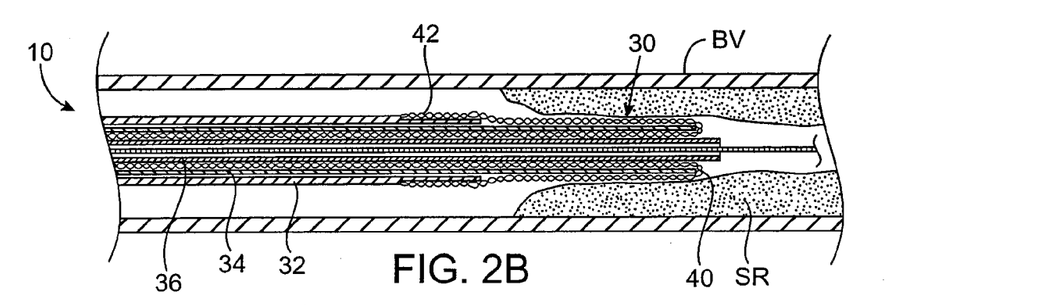

At that point, the prosthesis 30 is advanced forwardly or distally into the stenosed region SR of the blood vessel BV, as shown in FIG. 2B. In particular, both the inner tube 36 and the middle tube 34 are advanced forwardly or distally relative to the outer tube 32. This causes the leading edge 40 of the prosthesis 30 to advance into the stenosed region SR, engaging and partially dilating the lumen wall within this region.

Figure 2C:
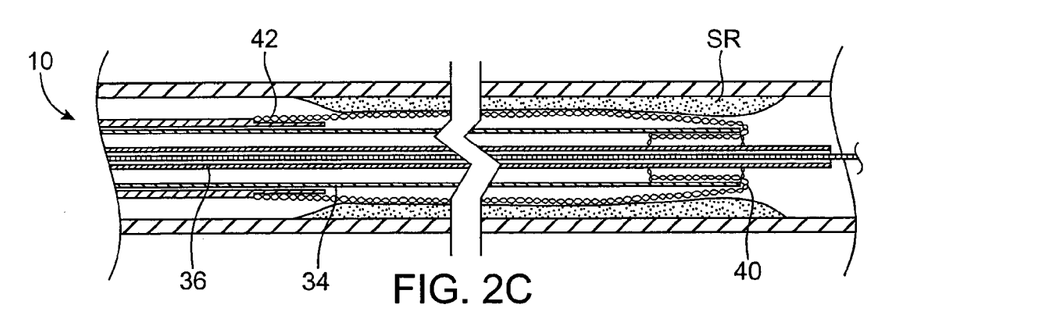

As the inner tube 36 and middle tube 34 are further advanced, as shown in FIG. 2C, the leading edge 40 of the prosthesis advances out through the other end of the stenosed region SR. During this entire deployment, fixed end 42 of the prosthesis has remained on the distal end of the outer tube 32 of the delivery catheter 10.

Figure 2D:
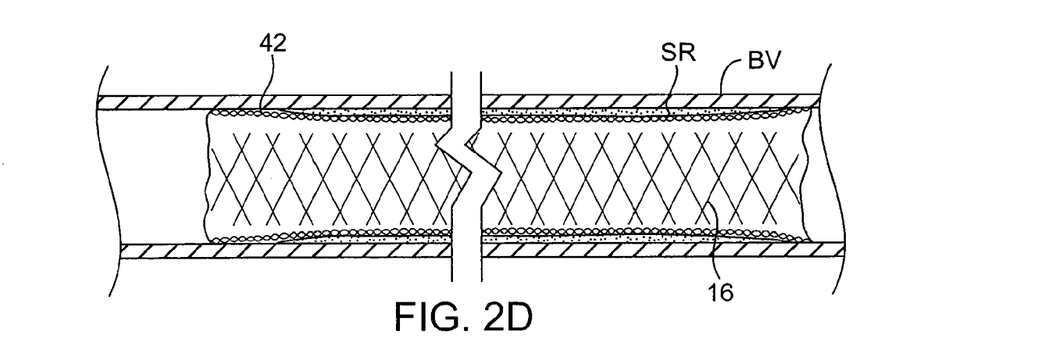

Once the prosthesis 30 is fully deployed, the outer tube 32 would be disengaged from the fixed end 42 of the prosthesis, e.g., by rotating or otherwise separating the catheter from the prosthesis, leaving the prosthesis 30 in place, as shown in FIG. 2D. As can be seen in FIG. 2D, the deployment of the prosthesis 30 has dilated the stenotic region. At this point, if the dilation is insufficient, or further anchoring of the prosthesis 30 is desired, a balloon or other expandable member may be expanded within the prosthesis 30 in a conventional manner. In one embodiment, for example, a balloon may be coupled with the outer tube 32 in such a way as to allow the balloon to be inflated to further anchor the prosthesis 30 in place.

It will be appreciated that the lengths, pitches, adjacent spacings, and the like, of the braided and other elements deployed according to the methods of the present invention can be controlled at the discretion of the treating physician. Thus, the methods and apparatus of the present invention provide useful flexibility for the treating physician to treat extended and disseminated disease in the vasculature and other body lumens.

Although the foregoing invention has been described in some detail by way of illustration and example, for purposes of clarity of understanding, it will be obvious that certain changes and modifications may be practices within the scope of the appended claims.

What is claimed is:

1. An apparatus for delivering a stent to a body lumen, said apparatus comprising:

an elongate flexible shaft having a proximal end, a distal end and a lumen therebetween;

self-expanding tubular stent having a sidewall defining a plurality of apertures therethrough, wherein the apertures are adapted to allow fluid flow therethrough, the stent carried in the flexible shaft lumen at least partially in a radially collapsed configuration and being separated into a first portion having a desired length for deployment and a second portion that remains in the flexible shaft lumen in the collapsed configuration after the apparatus has been removed from the body lumen, wherein upon deployment the first portion is radially expanded into an expanded configuration everted relative to the collapsed configuration;

a slidable member adjacent the flexible shaft for advancing the stent from the flexible shaft lumen so that said stent radially expands into engagement with an inner wall of the body lumen and applies a radially outward force against the inner wall; and a separation element adjacent the flexible shaft, the separation element adapted to separate the stent into the first portion which is released from the flexible shaft so as to remain in the body lumen while the second portion remains disposed at least partially in the flexible shaft lumen after the apparatus has been removed from the body lumen.

2. The apparatus of claim 1, wherein the stent comprises a braided stent.

3. The apparatus of claim 1, wherein the stent comprises a patterned thin wall tube.

4. The apparatus of claim 1, wherein the stent comprises a metallic structure.

5. The apparatus of claim 1, wherein the-stent comprises a nickel titanium alloy.

6. The apparatus of claim 1, wherein the stent carries a therapeutic agent adapted to be released therefrom in a controlled manner.

7. The apparatus of claim 6, wherein the therapeutic agent inhibits restenosis.

8. The apparatus of claim 1, further comprising an expandable member disposed on the flexible shaft near the distal end.

9. The apparatus of claim 8, wherein the expandable member comprises a balloon.

10. The apparatus of claim 1, wherein the stent everts as it is advanced from the flexible shaft lumen.

11. The apparatus of claim 1, wherein the separation element comprises a severing element adapted to sever the stent into the first portion and the second portion.

12. A method for delivering a stent to a body lumen, said method comprising:

positioning a delivery catheter carrying self-expanding tubular stent having a sidewall defining a plurality of apertures therethrough adapted to allow fluid flow therethrough, to a target site within the body lumen, the stent being into a first portion having a desired length for deployment and a second portion that remains carried within the delivery catheter after the delivery catheter has been removed from the body lumen;

advancing the stent from the delivery catheter into the body lumen;

radially expanding the first portion of the stent from a contracted state to an expanded state, wherein in the expanded state the expanded first portion of the stent is in engagement with an inner wall of the body lumen so as to apply a radially outward force against the inner wall, and wherein the expanded first portion is everted relative to the second portion;

separating the stent into the first portion and the second portion; and releasing the first portion into the target site while the second portion of the stent remains carried within the delivery catheter after the delivery catheter has been removed from the body lumen.

13. The method of claim 12, wherein the step of separating comprises severing the stent.

14. The method of claim 13, wherein the severing comprises severing the stent with a severing member coupled to the delivery catheter.

15. The method of claim 12, further comprising releasing a therapeutic agent from the first portion after deployment thereof.

16. The method of claim 15, wherein the therapeutic agent inhibits restenosis.

17. The method of claim 12, wherein the step of positioning the delivery catheter comprises carrying the stent in a radially collapsed configuration.

18. The method of claim 12, further comprising expanding an expandable member within the first portion so as to anchor the desired length into the body lumen.

19. The method of claim 18, wherein expanding the expandable member comprises inflating a balloon coupled to the delivery catheter.

20. The method of claim 12, wherein advancing the stent comprises everting the stent so that an inside surface is exposed radially outwardly and advanced over a desired length of a wall of the body lumen.

21. The method of claim 20, wherein the step of everting comprises pushing the stent from the delivery catheter.

22. The method of claim 12, wherein the body lumen is a blood vessel.

23. The method of claim 12, wherein the stent comprises a braided stent.

24. The method of claim 12, wherein the stent comprises a patterned thin wall tube.

* * * * *